(12) United States Patent
Toki et al.

(10) Patent No.: US 7,238,864 B2
(45) Date of Patent: Jul. 3, 2007

(54) ACETOLACTATE SYNTHASE GENE PROMOTER

(75) Inventors: Seiichi Toki, Ibaraki (JP); Hiroaki Ichikawa, Ibaraki (JP); Hidemitsu Nakamura, Ibaraki (JP); Kiyoshi Kawai, Tokyo (JP); Koichiro Kaku, Tokyo (JP); Tsutomu Shimizu, Tokyo (JP)

(73) Assignees: Kumiai Chemical Industry Co., Ltd., Tokyo (JP); National Institute of Agrobiological Sciences, Tsukuba-Shi (JP)

( * ) Notice: Subject to any disclaimer, the term of this patent is extended or adjusted under 35 U.S.C. 154(b) by 0 days.

(21) Appl. No.: 11/075,808

(22) Filed: Mar. 10, 2005

(65) Prior Publication Data

US 2005/0241021 A1    Oct. 27, 2005

(30) Foreign Application Priority Data

Mar. 12, 2004  (JP)  ............................. 2004-071462
Mar. 4, 2005  (JP)  ............................. 2005-061036

(51) Int. Cl.
*C07H 21/04*  (2006.01)
*C12N 5/05*  (2006.01)
*C12N 15/09*  (2006.01)
*A01H 1/00*  (2006.01)
*A01H 5/00*  (2006.01)

(52) U.S. Cl. .................. 800/295; 435/320.1; 435/419; 435/468; 536/24.1; 800/278; 800/300

(58) Field of Classification Search ..................... None
See application file for complete search history.

(56) References Cited

OTHER PUBLICATIONS

Kim et al. (Plant Molecular Biology, 24:105-117, 1994).*
Sasaki et al. (NCBI, GenBank, Sequence Accession No. AP005841, pp. 1-53, Published in NCBI database in 2002).*
Li et al. (Plant Physiol., 100:662-668, 1992).*

* cited by examiner

*Primary Examiner*—Phuong T Bui
*Assistant Examiner*—Vinod Kumar
(74) *Attorney, Agent, or Firm*—Birch Stewart Kolasch & Birch, LLP

(57) ABSTRACT

The present invention provides methods for inducing tissue-specific expression, which includes preparing an expression vector having a promoter. The promoter includes any one of the following DNAs (a) to (c): (a) a DNA, which includes the nucleotide sequence shown in SEQ ID NO: 1; (b) a DNA, which includes the nucleotide sequence ranging from nucleotides 1344 to 2843 of SEQ ID NO: 1; and (c) a DNA, which is a DNA fragment that can hybridize under stringent conditions to a DNA fragment including a nucleotide sequence fully complementary to the nucleotide sequence shown in SEQ ID NO: 1, wherein (a), (b) or (c) can control the transcription of a coding sequence located downstream thereof; and wherein the stringent conditions are 5×SSC at 42° C.; The expression vector, also, includes a coding sequence located downstream of the promoter. Additionally, the method includes introducing the expression vector into a plant cell to obtain a transgenic plant; wherein the promoter activity is lower in mature seeds or root bases than in plant tissues other than mature seeds or root bases. The present invention also provides transformants containing a promoter; the promoter includes any of the DNAs (a) to (c) described above.

7 Claims, 7 Drawing Sheets
(2 of 7 Drawing Sheet(s) Filed in Color)

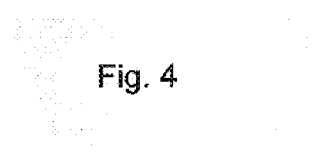
Fig. 4
Fig. 5
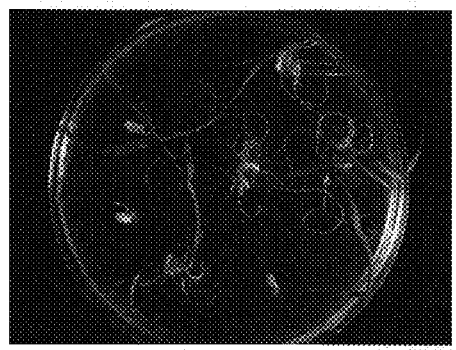
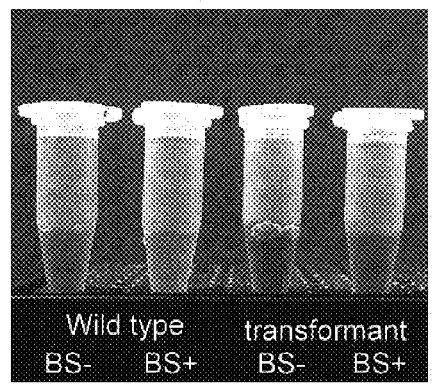

root　　　　　　　　　　stem　　　　　　　　　　leaf

ACETOLACTATE SYNTHASE GENE PROMOTER

FIELD OF THE INVENTION

The present invention relates to a novel promoter that can be used to produce a transformed plant and a method for specifically expressing a gene in predetermined tissue in a plant using the promoter.

BACKGROUND OF THE INVENTION

Gene expression in eukaryotes is induced at a region of a DNA sequence referred to as a promoter. Generally, a promoter is located upstream of codon regions, has a binding site for RNA polymerase, and controls the transcriptional initiation of DNA located downstream thereof. The promoter region also contains other elements functioning as regulatory genes for gene expression. The promoter region has a TATA box consensus sequence at position approximately −30 bp on the 5' end from the initiation codon and often has a CAAT box consensus sequence at position approximately −75 bp from the same (Breathnach and Chambon (1981) Ann. Rev. Biochem. 50: 349–383 (non-patent document 1); Messing et al., Genetic Engineering of Plants, T. Kosuge, Meredish and Hollaender (ed), pp. 211–227 (1983) (non-patent document 2)).

In plants, the CAAT box may be substituted with a consensus sequence located at the same distance as that of the CAAT box from a cap site, which is named the AGGA box by Messing et al. (non-patent document 2). Transcription is initiated when a transcriptional factor (protein) binds to the TATA box consensus sequence. Next, at the signal of this binding, RNA polymerase and other transcriptional factors bind, initiating transcription from the transcription initiation point. When RNA polymerase reaches a terminator indicating transcription termination, transcription is completed. A promoter is a binding site for RNA polymerase and also regulates the direction in which an enzyme moves over DNA. Hence, which one of the double strands becomes a template strand is determined depending on the position of a promoter. Efficient expression of a gene introduced into a plant cell is an important issue in the production of transgenic plants. A promoter sequence is a major factor in determining the transcriptional level of a gene within a plant cell. Generally, the use of a promoter sequence with strong transcriptional activity enables improvement of the expression level of a target gene. It is known that in promoter sequences, there are specificities based on differences in RNA polymerases that differ depending on plant species, organs, tissues, cells, or environmental conditions. Therefore, to carry out gene expression in a plant cell, it is necessary to use a promoter sequence that functions under purpose conditions.

Conventionally, examples of promoters capable of functioning within plants include a 35S promoter (EP0131623 (patent document 1)) derived from a cauliflower mosaic virus (CaMV), promoters (nopaline synthase (nos) and mannopine synthase (mas)) that can be found in Agrobacterium T-DNA, and an octopine synthase (ocs) promoter (EP0122791 (patent document 2), EP0126546 (patent document 3), and EP0145338 (patent document 4)).

However, it is known that dicotyledons and monocotyledons differ in their transcription efficiency. It has been reported that although CaMV-derived 35S promoter is a strong promoter that causes high-level RNA production in a wide variety of types of plants, including plants that are far from the viral host range, the 35S promoter has only relatively low activity in agriculturally important gramineous plants (Shimamoto et al., 1989 Nature 338, 274–276 (non-patent document 3); Rhodes et al., 1988 Science 240, 204–207 (non-patent document 4)). In a promoter of a monocotyledon, introns are present in the 5' untranslation region of a gene to be induced thereby, and these are absent in dicotyldons and are necessary for activating thereby, and these are absent in dicotyldons and are necessary for activating gene expression. Hence, it is often impossible to obtain effective expression levels by simple ligation thereof. Therefore, in monocotyledons, improvement of the 5' untranslation region, use of introns, and gene resynthesis have been devised to increase expression levels (Plant Mol. Biol. 32 (1996) 393–405 (non-patent document 5); Plant Cell Rep. 6: 265–270 (non-patent document 6)). According to other studies, Kay et al., (Science 236: 1299–1302 (1987) (non-patent document 7)) have reported transcriptional activity that is ten times higher in tobacco plants that had experienced gene transfer and that had a CaMV-derived 35S promoter. They have also reported that the CaMV-derived 35S promoter upstream sequence of 260 bp was contained twice.

Furthermore, Ow et al., (Proc. Natl. Acad. Sci. 84: 4870–4874 (1987) (non-patent document 8)) have reported that multimeric structure of the terminal region of a 35S promoter (between positions −148 and −89) can activate a 35S promoter core to an expression level higher than that obtained by a natural 35S promoter. Furthermore, Fang et al., (The Plant Cell 1: 141–150 (1989) (non-patent document 9)) have reported that monomeric structure and multimeric structure of upstream 35S promoter fragments (between −209 and −46) can act as enhancers to increase transcription from heterologous promoters. In these studies, 8 repeats of the upstream region between positions −209 and −46 of a 35S promoter have been cloned at position −50 of an rbcS-3A gene, which is a small subunit of ribulosebisphosphate carboxylase. The octamer increased rbcS-3A transcription to levels higher than those obtained using an rbcS-3A upstream region (non-patent document 9).

Under such circumstances, it is extremely important to provide a promoter having strong activity for molecular breeding of plants using transformation methods. The importance of a promoter that functions efficiently, particularly in monocotyledons to which major grains such as rice, wheat, and corn belong, is particularly high. Hence, as promoters derived from monocotyledons, the use of several examples including a rice actin promoter (U.S. Pat. No. 5,641,876 (patent document 5)) and a corn ubiquitin promoter (U.S. Pat. No. 5,510,474 (patent document 6)) has been attempted.

In addition, acetolactate synthase (ALS) is a common enzyme at the initial stage of the branched amino acid biosynthetic pathway that is present in plants and microorganisms. It is known as a target enzyme of at least four structurally different herbicides (including sulfonylureas, imidazolinones, triazolopyrimidinesulfonamides, and pyrimidinecarboxy herbicides). In addition, acetolactate synthase (ALS) is not present in animals, so that these herbicides have a slight effect on human bodies. Moreover, the nucleotide sequence of ALS gene is highly conserved, particularly in plants (Mazur et al., Annu Rev Plant Physiol 40 441–447 (1987) (non-patent document 10)). Gail et al. (Pesticide Sci. 30(4) 418–419 (1990) (non-patent document 11)) have examined expression of acetolactate synthase (ALS) in various tissues including leaves, stems, roots, flowers, pods, and meristems by enzyme assay using Lima beans. ALS activity was measured on days 14, 28, and 42 after sowing in leaves, stems, roots, and meristems, and ALS activity was measured on day 42 after sowing in flowers and pods. Gail et al. have reported that the activity decreased with aging in tissues other than stems, but ALS was expressed constitutively in any tissue. Sharon J. Keeler et al. have observed the constitutive expression of ALS in various tobacco tissues including seedlings, leaves, stems, roots, and flowers (Plant Physiol. 102, 1009–1018 (1993) (non-patent document 12)). ALS expression was shown to be highest in developing organs such as seedlings and young leaves and lowest in mature leaves. Also, in the results of in situ hybridization, the highest ALS expression was observed in metabolically active cells of roots, stems, and flowers or dividing cells. For example, in roots, expression was highest in the tips of the roots. The further the distance from the tips (that is, the older the cells), the gradually lower the expression. Regarding the transcription products of ALS, expression of approximately 0.1% of all mRNA was observed and a maximum 4-fold difference was observed in expression levels among tissues.

[Patent Document 1] EP 0131623
[Patent Document 2] EP 0122791
[Patent Document 3] EP 0126546
[Patent Document 4] EP 0145338
[Patent Document 5] U.S. Pat No. 5,641,876
[Patent Document 6] U.S. Pat. No. 5,510,474
[Non-patent Document 1] Breathnach and Chambon (1981) Ann. Rev. Biochem. 50: 349–383
[Non-patent Document 2] Messing et al., Genetic Engineering of Plants, T. Kosuge, Meredish and Hollaender (ed), pp. 211–227 (1983)
[Non-patent Document 3] Shimamoto et al., 1989 Nature 338, 274–276
[Non-patent Document 4] Rhodes et al., 1988 Science 240, 204–207
[Non-patent Document 5] Plant Mol. Biol. 32 (1996) 393–405
[Non-patent Document 6] Plant Cell Rep. 6: 265–270
[Non-patent Document 7] Science 236: 1299–1302 (1987)
[Non-patent Document 8] Proc. Natl. Acad. Sci. 84: 4870–4874 (1987)
[Non-patent Document 9] The Plant Cell 1: 141–150 (1989)
[Non-patent Document 10] Mazur et al., Annu Rev Plant Physiol 40 441–447
[Non-patent Document 11] Pesticide Sci. 30(4) 418–419 (1990)
[Non-patent Document 12] Plant Physiol. 102, 1009–1018 (1993)

SUMMARY OF THE INVENTION

In plants, as described above, various promoters for controlling gene expression have been reported. However, practically usable promoters are limited and promoters that can enable characteristic gene expression control have been awaited.

Hence, in view of such circumstances, it is an object of the present invention to provide a novel promoter that enables characteristic gene expression control and a method for specifically expressing a gene in a predetermined tissue in a plant body using the promoter.

The present invention that has achieved the above object encompasses the following (1) to (10).

(1) A promoter, which comprises any one of the following DNAs (a) to (c):

(a) a DNA, which comprises the nucleotide sequence shown in SEQ ID NO: 1;
(b) a DNA, which comprises a nucleotide sequence derived from the nucleotide sequence shown in SEQ ID NO: 1 by deletion, substitution, insertion, or addition of 1 or a plurality of nucleotides, and which can control the transcription of a gene located downstream thereof; and
(c) a DNA, which is a DNA fragment that can hybridize under stringent conditions to a DNA fragment comprising a nucleotide sequence complementary to the nucleotide sequence shown in SEQ ID NO: 1, and which can control the transcription of a gene located downstream thereof.

(2) The promoter of (1), the activity thereof being lower in seeds than that in plant tissues other than seeds.
(3) The promoter of (1), which shows activity only in plant tissues other than seeds.
(4) The promoter of (1), the activity thereof being lower in roots than that in plant tissues other than roots and seeds.
(5) The promoter of (1), the activity thereof being higher in meristems than that in plant tissues other than seeds.
(6) An expression vector, which comprises the promoter of any one of (1) to (5).
(7) The expression vector of (6), which comprises a gene downstream of the above promoter.
(8) A transformant, which is prepared by introducing the expression vector of (6) or (7) into a host cell.
(9) The transformant of (8), which is a transgenic plant.
(10) A method for inducing tissue-specific expression, which comprises specifically inducing expression of a gene located downstream of the above promoter in plant tissues other than seeds by culturing the transformant of (9).
(11) The method for inducing tissue-specific expression of (10), wherein the gene located downstream of the above promoter is a drug-resistant acetolactate synthase gene.

The present invention is explained in detail by referring to drawings as follows.

The promoter according to the present invention is a DNA region derived from DNA located (in a direction from the 5' terminus to the 3' terminus) upstream of a rice-derived acetolactate synthase gene (hereinafter referred to as an ALS gene). This promoter has a DNA fragment consisting of the nucleotide sequence shown in SEQ ID NO: 1 and can control transcription of a gene located downstream thereof (in a direction from the 3' terminus to the 5' terminus).

The promoter according to the present invention is not limited to such a promoter having the DNA fragment consisting of the nucleotide sequence shown in SEQ ID NO: 1, and may also be a DNA fragment that comprises a nucleotide sequence derived from the nucleotide sequence shown in SEQ ID NO: 1 by deletion, substitution, insertion, and addition of 1 or a plurality of nucleotides and that is able to control transcription of a gene located downstream thereof. Here, a plurality of nucleotides means 1 to 200, preferably 1 to 100, and more preferably 1 to 50 continuous or discontinuous nucleotides.

Furthermore, the promoter according to the present invention may also be a DNA fragment that can hybridize under stringent conditions to a DNA fragment comprising a nucleotide sequence complementary to the nucleotide sequence shown in SEQ ID NO: 1 and that is able to control transcription of a gene located downstream thereof. Here, the stringent conditions include a sodium concentration between 25 mM and 500 mM, and preferably between 25 mM and 300 mM, and temperature between 42° C. and 68° C., and preferably between 42° C. and 65° C. More specifically the stringent conditions include 5×SSC (83 mM NaCl and 83 mM sodium citrate) and temperature of 42° C.

Whether or not a DNA fragment comprising a nucleotide sequence differing from that shown in SEQ ID NO: 1 functions as a promoter can be determined by constructing (see below) an expression vector so that a reporter gene is located downstream of the DNA fragment, and then confirming expression of the reporter gene in a plant cell or a plant body that has been transformed with the expression vector. Here, as a reporter gene, a GUS gene, a luciferase gene, a green fluorescent protein gene, or the like can be used.

Furthermore, the promoter according to the present invention may also be a DNA fragment comprising a region between nucleotides 1344 and 2843 in the nucleotide sequence shown in SEQ ID NO: 1. That is, since the region between nucleotides 1344 and 2843 of the nucleotide sequence shown in SEQ ID NO: 1 is considered to be an important region for exerting functions, particularly functions as a promoter, this region alone functions as a promoter.

Specifically, according to results of searches conducted on the nucleotide sequence shown in SEQ ID NO: 1 using a Place program for predicting plant transcriptional regulatory factors (see Nucleic Acids Research Vol. 27 No.1 pp. 297–300) and a TFBIND program for transcriptional factor binding site searches using unique thresholds (by RIKEN SNP Research Center; see BIOINFORMATICS, Vol.15, No.7/8, pp. 622–630, 1999), important motifs for a promoter sequence, such as a TATA box, a CAAT box, and a CCAAT box, are recognized within approximately 1.5 kbp (nucleotides 1344 to 2843 of the nucleotide sequence shown in SEQ ID NO: 1) upstream of the ALS gene translation initiation point (ATG). More specifically, in the nucleotide sequence shown in SEQ ID NO: 1, a CAAT box is present in a region between nucleotides 1672 and 1675 and a TATA box is present in the vicinity approximately 45 bp downstream as predicted from the presence of a CAAT box; that is, in a region between nucleotides 1710 and 1716. Furthermore, a CCAAT box that is known to enhance promoter activity was present in a region between nucleotides 1421 and 1425, a region between nucleotides 1501 and 1505, a region between nucleotides 2196 and 2200, and a region between nucleotides 2606 and 2610 in the nucleotide sequence shown in SEQ ID NO: 1. Furthermore, most motifs recognized by the CaMV-derived 35S promoter are present in a region between nucleotides 1344 and 2843 in the nucleotide sequence shown in SEQ ID NO: 1. Based on the above studies, the region between nucleotides 1344 and 2843 in the nucleotide sequence shown in SEQ ID NO: 1 can be said to be a region particularly important for functions as a promoter.

The promoter according to the present invention controls transcription of a gene located downstream thereof so as to express the gene in a plant-tissue-specific manner. Specifically, the promoter has a first feature of showing extremely low activity in seeds; that is, it does not substantially show activity in seeds. Here, "not substantially showing activity" means, for example, activity at a level where expression of a reporter gene is undetectable in seeds that are obtained by producing a transformed plant using an expression vector in which the reporter gene has been incorporated downstream of a promoter and then collecting the seeds from the transformed plant.

Furthermore, this promoter has a second feature of showing extremely low activity in roots. Here, "extremely low activity" means activity that is extremely low when compared with activity in plant tissues other than roots and seeds. Examples of tissues other than roots include plant organs such as leaves, flower petals, and stems and plant tissues such as epidermis, phloem, parenchyma, xylem, and fibrovascular bundles.

Furthermore, this promoter has a third feature of having activity in meristems that is higher than that in plant tissues other than seeds. Here, "meristems" means tissues or parts where cell division actively proceeds. Examples of meristems include apical meristems (shoot apex meristems and root apical meristems), lateral meristems (cambium and phellogen), and germ cells.

Moreover, the expression vector according to the present invention is a basic vector having the above promoter incorporated therein. It is preferable that such an expression vector have a region located downstream of the promoter for incorporation of a gene to be subjected to expression control by the promoter. In addition, the expression vector may also be a vector in which a gene to be subjected to expression control has been previously incorporated downstream of the promoter.

The basic vector is not specifically limited, as long as it is replicable in a host. Examples of such a basic vector include plasmids, shuttle vectors, and helper plasmids. Examples of plasmid DNAs include plasmids derived from *Escherichia coli* (e.g., pBR322, pBR325, pUC118, pUC119, pUC18, pUC19, and pBluescript), plasmids derived from *Bacillus subtilis* (e.g., pUB110 and pTP5), and plasmids derived from yeast (e.g., YEp13 and YCp50). Examples of a phage DNA include λ phage (Charon4A, Charon21A, EMBL3, EMBL4, λgt10, λgt11, and λZAP). Furthermore, animal virus such as retrovirus or vaccinia virus and an insect virus vector such as baculovirus can also be used.

According to a method that is employed herein, to insert the above-described promoter into a basic vector, the promoter is isolated by digesting a purified rice chromosomal DNA with an appropriate restriction enzyme. Alternatively, the promoter is isolated by polymerase chain reaction using a purified rice chromosomal DNA as a template. Then, the thus isolated promoter is inserted into a restriction enzyme site or a multi-cloning site of an appropriate vector for ligation.

In the present invention, to express an arbitrary gene, the arbitrary gene can be further inserted into the above expression vector. The technique for inserting an arbitrary gene is similar to that for inserting a promoter into a vector. The arbitrary gene is not specifically limited.

A target arbitrary gene is connected in the sense or the antisense direction to the above promoter, and then the thus prepared promoter can also be inserted into a vector such as pBI101(Clontech), referred to as a binary vector.

In the meantime, a plant can be transformed using the expression vector according to the present invention. That is, a transformant (transformed plant) can be produced utilizing the expression vector according to the present invention. Specifically, a transformant can be obtained by introducing an expression vector having a desired gene introduced therein into a host. As a host, which is not specifically limited as long as it can express a promoter and a target gene, a plant is preferable. As a plant, monocotyledons are preferable, and they are represented by corn (*Zea mays*) and rice (*Oryza saliva*). Other examples of a plant to be used for transformation include plants belonging to the family Brassicaceae, the family Solanaceae, the family Leguminosae, or the like (see below), but examples are not limited thereto.

Family Brassicaceae: *Arabidopsis* (*Arabidopsis thaliana*)
Family Solanaceae: Tobacco (*Nicotiana tabacum*)

Family Leguminosae: Soybean (*Glycine max*)

The above expression vector can be introduced into a plant cell by a general transformation method, such as an electroporation method, an Agrobacterium method, a Particle gun method, or a PEG method.

For example, when the electroporation method is employed, electroporation is carried out under conditions where a voltage ranges from 500 V to 1600 V, 25 µF to 1000 µF, and 20 msec to 30 msec using an electroporation system equipped with a pulse controller, so as to introduce an expression vector into a host.

Moreover, when the particle gun method is employed, plant bodies, plant organs, and plant tissues may also be directly used, used after preparation of sections thereof, or used after preparation of protoplasts. The thus prepared samples can be treated using a gene transfer system (e.g., PDS-1000/He of Bio-Rad). Treatment conditions differ depending on plants or samples. In general, treatment is carried out with pressure ranging from approximately 1000 psi to 1800 psi at a distance ranging from approximately 5 to 6 cm.

Furthermore, by utilizing a plant virus as a basic vector, a target gene under control of the above promoter can be introduced into a plant body. An example of a plant virus that can be utilized herein is a cauliflower mosaic virus. Specifically, first, a viral genome is inserted into, for example, a vector derived from *Escherichia coli* to prepare a recombinant, and then target genes are inserted into the genome of a plant virus having the above promoter. The thus modified viral genome is excised from a recombinant using a restriction enzyme and then inoculated in a plant host, so that the above promoter and target gene can be introduced into the plant host.

In the method utilizing a Ti plasmid of *Agrobacterium*, through the utilization of a property whereby bacteria belonging to the genus *Agrobacterium* transfer portions of their plasmid DNAs into the plant genome when they infect a plant, the above promoter and target gene are introduced into a plant host. Of bacteria belonging to the genus *Agrobacterium*, *Agrobacterium tumefaciens* infects a plant to form a tumor referred to as crown gall and *Agrobacterium rhizogenes* infects a plant to cause generation of hairy roots. Such phenomena are caused when a region referred to as a T-DNA region (Transferred DNA) on a plasmid that is referred to as a Ti plasmid or an Ri plasmid and is present in each bacterium is transferred into a plant upon infection, and then incorporated into the plant genome.

By previous insertion of a gene to be incorporated into a plant genome and the above promoter into a T-DNA region on the Ti or the Ri plasmid, the target DNA and the promoter can be incorporated into the plant genome when bacteria belonging to the genus *Agrobacterium* infect the plant host.

Tumor tissues, shoots, hairy roots, and the like obtained as a result of transformation can be directly used for cell culture, tissue culture, or organ culture. In addition, they can be caused to regenerate into plant bodies by a conventionally known plant tissue culture method that involves administration of a plant hormone (e.g., auxin, cytokinin, gibberellin, abscisic acid, ethylene, and brassinolide) in an appropriate concentration, or the like.

In addition, the above-mentioned expression vector is introduced into not only the above plant hosts, but also bacteria belonging to the genus *Escherichia* such as *Escherichia coli*, the genus *Bacillus* such as *Bacillus subtilis*, or the genus *Pseudomonas* such as *Pseudomonas putida*; yeast such as *Saccharomyces cerevisiae* or *Schizosaccharomyces pombe*; animal cells such as COS cells or CHO cells; or insect cells such as Sf9, so that transformants can also be obtained. When bacteria such as *Escherichia coli* or yeast are used as hosts, the expression vector of the present invention is preferably capable of autonomous replication in the bacteria. At the same time, the vector is composed of the above promoter, a ribosome binding sequence, a target gene, and a transcription termination sequence. In addition, the expression vector may also contain a gene under the control of the above promoter.

A method for introducing an expression vector into bacteria is not specifically limited, as long as it is a method for introducing DNA into bacteria. Examples of such a method include a method using calcium ions and an electroporation method.

When yeast is used as a host, for example, *Saccharomyces cerevisiae* and *Schizosaccharomyces pombe* are used. A method for introducing an expression vector into yeast is not specifically limited, as long as it is a method for introducing DNA into yeast. Examples of such a method include an electroporation method, a spheroplast method, and a lithium acetate method.

When animal cells are used as hosts, monkey cells (COS-7 or Vero), Chinese hamster ovary cells (CHO cells), mouse L cells, or the like are used. Examples of a method for introducing an expression vector into animal cells include an electroporation method, a calcium phosphate method, and a lipofection method.

When insect cells are used as hosts, Sf9 cells or the like are used. Examples of a method for introducing an expression vector into insect cells include a calcium phosphate method, a lipofection method, and an electroporation method.

Whether or not a gene is incorporated into a host can be confirmed by the PCR method, the Southern hybridization method, the Northern hybridization method, or the like. For example, DNA is prepared from a transformant, DNA-specific primers are designed, and then PCR is carried out. Subsequently, amplification products are subjected to agarose gel electrophoresis, polyacrylamide gel electrophoresis, or capillary electrophoresis, stained with ethidium bromide, an SYBR Green solution, or the like, and then detected as a single band, thereby confirming transformation. Furthermore, amplification products can also be detected by PCR using primers previously labeled with a fluorescent dye or the like. Furthermore, a method that can also be employed for confirming amplification products involves binding amplification products to a solid phase such as a micro-plate, and then confirming the products by fluorescence reaction, enzyme reaction, or the like.

The above transformed plant cells can be regenerated into transformed plant bodies. As a regeneration method, a method for obtaining complete plant bodies, which involves transferring and culturing callus-shaped transformed cells in media varying in hormone type and concentration to cause the cells to form adventitious embryos, is employed. Examples of media used herein include LS media and MS media.

Plant seeds are obtained from the regenerated transformed plants, and then plant bodies can also be produced from the plant seeds. The thus produced plant bodies contain the above promoter and a gene whose expression is controlled by the promoter.

To obtain plant seeds from transformed plants, for example, transformed plants are collected from rooting media and then transplanted into pots containing soil containing water. The plants are grown at a constant temperature for the plants to form flowers, and then the plants are finally caused to form seeds. In addition, to produce plant bodies from seeds, for example, when seeds formed by transformed plants mature, the seeds are isolated, inoculated in soil containing water, and then grown at a constant temperature and illumination.

As described above, the promoter according to the present invention can be broadly used as a novel and strongly functioning promoter for plants, such as when plant character is transformed by gene transfer.

As an example, when plants are transformed by incorporation of two or more genes for plant expression therein, it is preferable to use different promoters for each gene for plant expression. This is because in the case of gene expression in plants, the so-called gene-silencing phenomenon has been reported concerning promoters (Park et al., The Plant Journal 9, 183–194 [1996]). The gene-silencing phenomenon entails the fact that the presence of 2 or more promoters of the same type in the same nucleus suppresses the transcription-promoting action.

Therefore, according to the present invention, there is an advantage in that a promoter that is particularly useful when plants are transformed can be provided. For example, when 2 or more genes are introduced into the same chromosome in a plant and when CaMV35S promoters that are generally often used as promoters to be ligated to various structural genes are used, the use of this single type of promoter may cause the gene-silencing phenomenon. In such a case, a promoter other than the CaMV35S promoter is necessary, and it is desired that it has ability almost equivalent to or above that of the CaMV35S promoter. When such a need arises, the promoter according to the present invention can be preferably used.

Furthermore, the promoter according to the present invention is a rice-derived promoter. Thus, it is quite unlikely that the promoter would exhibit behavior unpredictable in plant bodies such as rice, unlike the cases of other plant-derived, microorganism-derived, or virus-derived promoters. Therefore rice having the promoter according to the present invention incorporated therein can be a practical plant that is more easily used in society.

Furthermore, since the promoter according to the present invention has the 1st feature of showing extremely low activity in seeds, the promoter can be used for regulating tissue-specific expression such that expression of a desired gene is suppressed in seeds but at the same time the gene is expressed in plant tissues other than seeds. Such a promoter that enables regulation of tissue-specific expression can be a very useful tool for experiments for analyzing gene functions and the like.

BRIEF DESCRIPTION OF THE DRAWINGS

The patent or application file contains at least one drawing executed in color. Copies of this patent or patent application publication with color drawing(s) will be provided by the office upon request and payment of the necessary fee.

In FIG. 2, portions indicated by arrows are mutation sites.

FIG. 4 is a photograph showing segregation of seeds obtained from $T_1$ generation on a selection medium containing 1 µM BS.

FIG. 5 is a photograph showing the result of confirmation of expression of an ALS gene by the in vivo ALS assay.

EXAMPLES

The present invention is further explained in detail using examples. However, the technical scope of the present invention is not limited by the following examples.

Example 1

Isolation Of ALS Gene

The full-length ALS cDNA from a Japonica type rice ALS gene has already been determined. As shown in the case of tobacco or Arabidopsis, the absence of introns in the rice ALS gene has been confirmed (Genbank accession AB049822). As a result of examining the Indica rice genome database (btn.genomics.org.cn/rice) using the rice ALS cDNA nucleotide sequence as a query, an 18-kbp contig sequence comprising 487 nucleotides of the 5' region of the rice ALS cDNA was discovered. When several oligonucleotide primers were synthesized based on the 18-kbp Indica type rice nucleotide sequence information and PCR was carried out, the 5' upstream 2.9-kbp fragment of the Japonica type rice (Nippon-bare) ALS gene was successfully amplified with a combination of 5'-tgggagaaaagggtcttagggtggacat-3' (SEQ ID NO: 2; primer located approximately 2.9 kbp upstream from the translation initiation point) and 5'-acgtg-gtgtcgctggtggttctta-3' (SEQ ID NO: 3; primer located approximately 60 bp downstream from the translation initiation point) primers.

Figure 1:
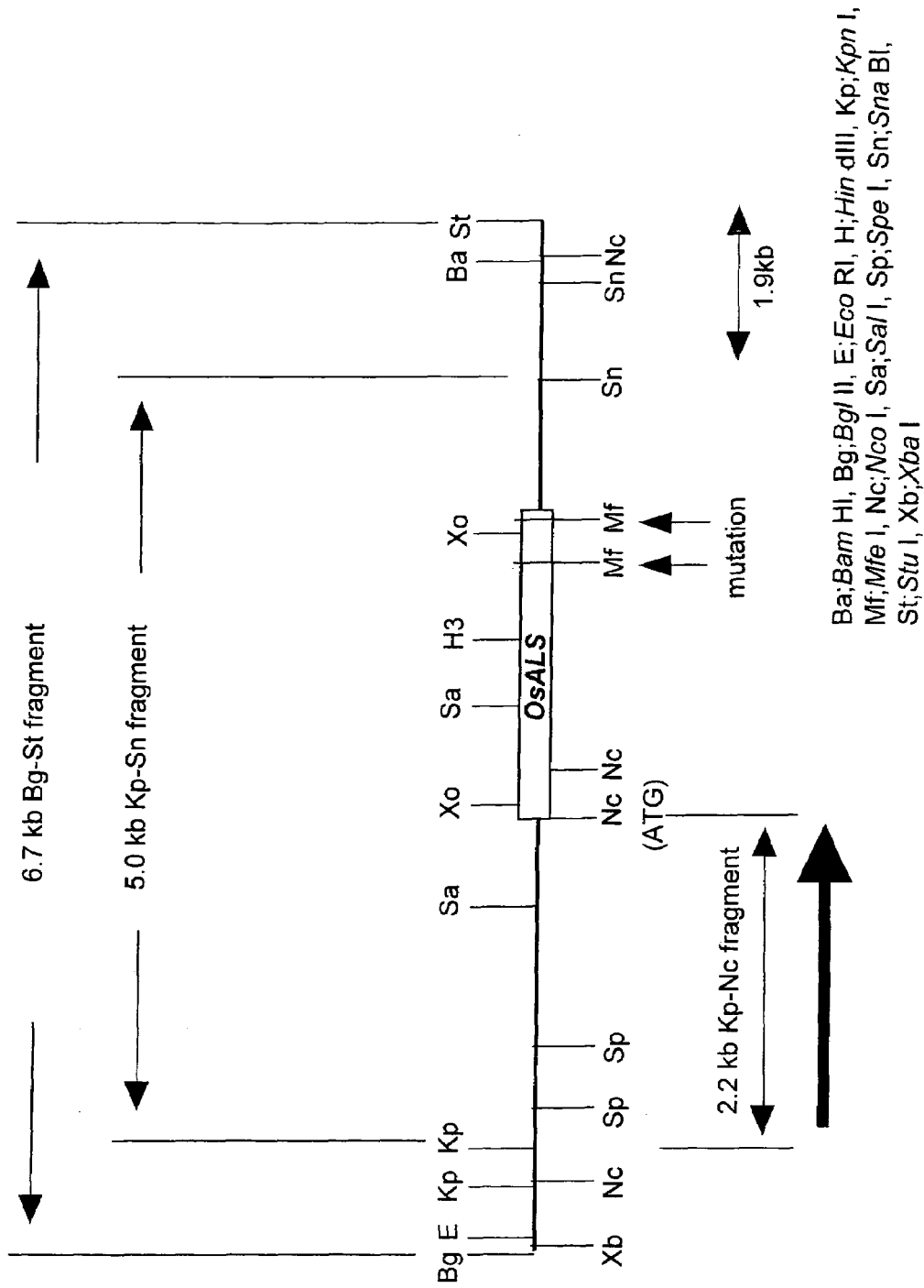
FIG. 1 is a schematic diagram showing an approximately 6.7-kbp fragment containing an approximately 2.8-kbp 5' upstream nucleotide sequence, an approximately 2.0-kbp coding sequence, and an approximately 1.9-kbp 3' downstream nucleotide sequence of an ALS gene (OsALS) amplified by PCR in Example 1.

In addition, an approximately 1.9-kbp 3' downstream nucleotide sequence of the rice ALS gene was cloned using a Universal Genome Walker kit (produced by Clontech). Finally, an approximately 6.7-kbp rice ALS genomic DNA comprising a 2.8-kbp 5' upstream nucleotide sequence (SEQ ID NO: 1), a 2.0-kbp coding sequence (SEQ ID NO: 4), and a 1.9-kbp 3' downstream nucleotide sequence (SEQ ID NO: 5) was amplified by the PCR method using Nippon-bare genomic DNA as a template. The PCR product was then cloned into pBluescript KS-(FIG. 1).

The thus cloned nucleotide sequence of the approximately 6.7-kbp fragment was determined and was compared with a sequence determined by direct sequencing of the PCR product. The 2.8-kbp 5' upstream nucleotide sequence is shown in SEQ ID NO: 1. An approximately 2.0-kbp coding sequence is shown in SEQ ID NO: 4. The 1.9-kbp 3' downstream nucleotide sequence is shown in SEQ ID NO: 5.

A BAC DNA nucleotide sequence (Genbank accession AP005841) containing rice ALS has been recently determined by the Rice Genome Research Program (RGP). When the BAC DNA nucleotide sequence was compared with the nucleotide sequence determined in this example, the two sequences were found to be completely identical.

In addition, the LITMUS28 plasmid that was constructed in this example to have an approximately 6.7-kbp fragment containing the 2.8-kbp 5' upstream sequence of the rice ALS gene cloned therein was deposited under accession number of FERM BP-08655 with the International Patent Organism Depositary, National Institute of Advanced Industrial Science and Technology (Chuo-5, 1-1-1, Higashi, Tsukuba-shi, Ibaraki, JAPAN) on Mar. 9, 2004, under the Budapest Treaty.

Example 2

Construction of Herbicide-resistance Rice ALS Gene and its Transformation

Figure 2:
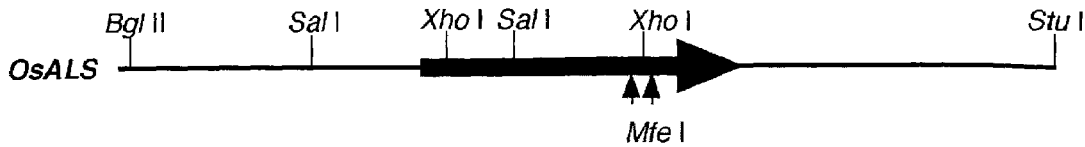
FIG. 2 is a schematic diagram showing a nucleotide sequence of an ALS gene (SEQ ID NO: 6), in which 2-point mutation was introduced.
Figure 3:
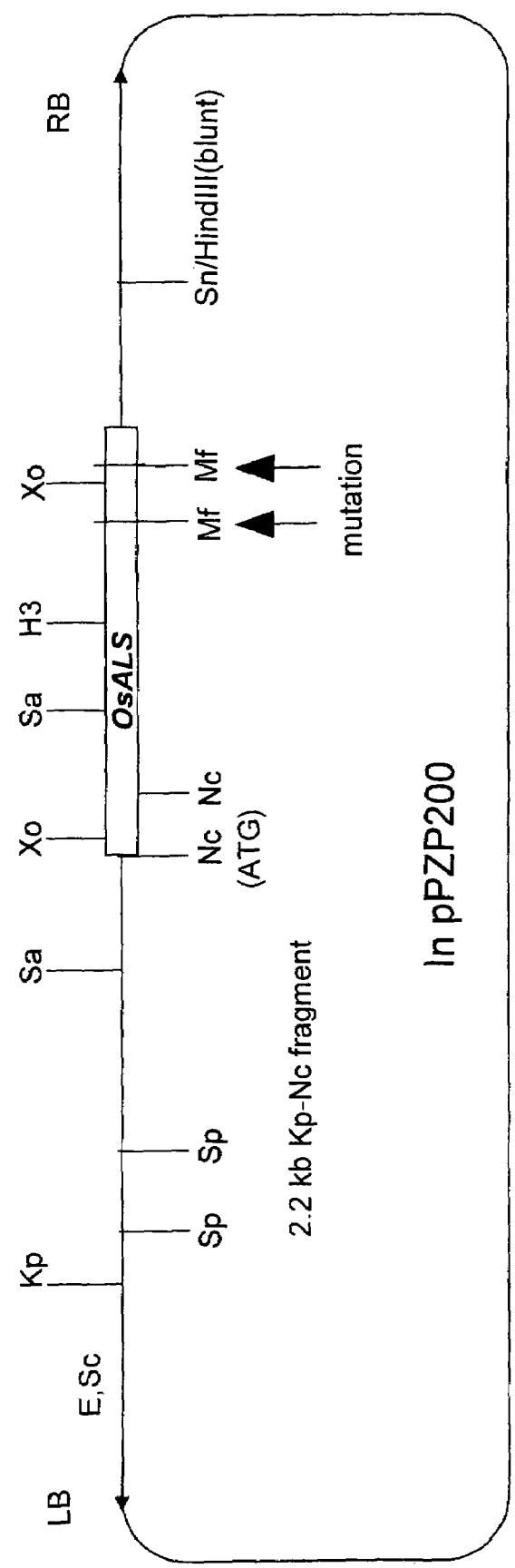
FIG. 3 is a schematic diagram showing a 5.0-kbp ALS gene fragment that was subcloned into the Kpn I/blunt-ended Hind III site of a pPZP200 binary vector.

A 5.0-kbp Kpn I/SnaB I DNA fragment comprising a 2.0-kbp nucleotide sequence of the rice ALS gene, a 2.2-kbp 5' upstream nucleotide sequence thereof, and a 0.8-kbp 3' downstream nucleotide sequence were subcloned into pBluescript KS-. A two-point mutated rice ALS gene was obtained by site-directed mutagenesis using a QuickChange Site-directed Mutagenesis Kit (produced by Stratagene), wherein triptophan 548 was mutated to leucine and serine 627 was mutated to isoleucine. As shown in FIG. 2, the two-point mutation provides two new Mfe I restriction enzyme sites to the rice ALS gene. The 5.0-kbp fragment of the herbicide-resistance ALS gene was further subcloned into a Kpn I/blunt-ended Hind III site of a pPZP200 binary vector (FIG. 3).

*Agrobacterium* mediated transformation of rice using pPZPOsALS(m) was performed according to the method reported by Toki (Plant Mol. Biol. Rep 15(1) 16–21, 1997). One week after transformation, infected calli were transplanted into a new medium containing 0.25 μM or 0.5 μM Bispyribac sodium salt (BS). Three weeks after transplantation, actively growing calli were transplanted again in media containing BS with the same concentration. After a further 3 weeks, calli actively growing on selection media were transplanted into regeneration media containing BS with the same concentration. The regenerated plants were further grown on hormone-free media to promote the growth of roots, and they were then transplanted into soil for maturation. Transformed plants of the $T_0$ generation were caused to self-pollinate. The thus obtained $T_1$ seeds were used for a herbicide resistance experiment. As shown in FIG. 4, seeds obtained from the transformed plants of the $T_1$ generation were segregated at a 3 (resistance): 1 (sensitive) ratio on a selection medium containing 1 μM BS. Hence, the phenotype of BS resistance was inherited as per Mendel's laws. Here, 6 out of 8 plants showed resistance.

We did not observe any abnormal segregation in the transformed plants of the $T_1$ generation. Hence, within the range of our tests, no gene-silencing or over-expression of a rice ALS gene occurred by transformation.

Example 3

Confirmation of Resistance of Rice Having an ALS-promoter-driven BS-resistance ALS Gene Introduced therein by the in Vivo ALS Assay.

After rice plants that had showed BS resistance on selection media were transplanted in soil and then grown to maturity, 150 mg of leaves were sampled, finely cut, and then put into a petri dish. A treatment solution (mixed salts for 25% MS media; 500 μM (final concentration) 1,1-cyclopropanedicarboxilic acid (CPCA); 5 μg Triton X-100; and 0.15 μM (final concentration) BS) was added to the dish, and the resultant was allowed to stand at 30 ° C. under light conditions (140001×) for 1 day. After reaction, the treated leaves were put into a 1.5 ml micro tube and then 200 μl of distilled water containing 0.025% Triton X-100 was added thereto. After the solution had been allowed to stand at 60° C. for 5 minutes, extraction was carried out with sonication (frequency of 40 kHz) for 15 minutes. 200 μl of the supernatant was transferred into another tube, 20 μl of 5% (v/v) sulfuric acid was added thereto, and then the resultant was allowed to stand at 60° C. for 30 minutes. Subsequently, 100 μl of a 0.5% (w/v) creatine and 100 μl of a 5% (w/v) 1-naphthol (prepared at the time of use) dissolved in a 2.5 N NaOH solution were added to the solution. The solution was allowed to stand at 37° C. for 30 minutes. A group of rice plants to which BS had been added showing resistance after 30 minutes also showed development of a red color similar to that developed by a group of rice plants to which no BS had been added (FIG. 5). It is understood that in the case of wild-type rice, the ALS gene was inhibited by addition of BS so that a red color was not developed.

Example 4

Analysis Of ALS Gene Promoter

Figure 6:
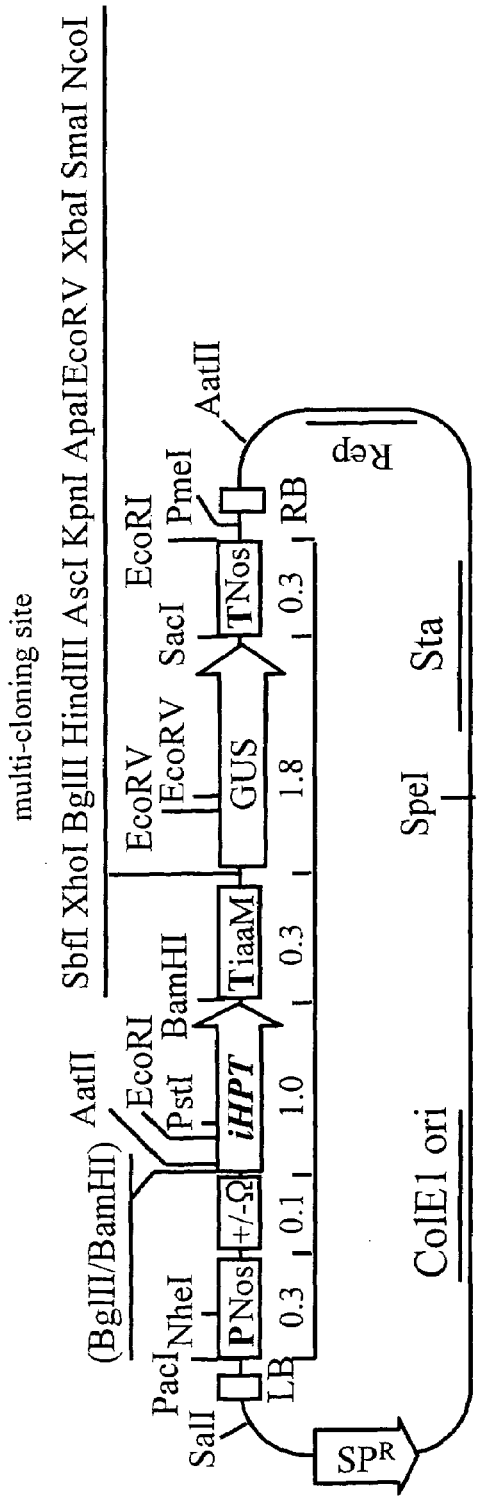
FIG. 6 is a schematic diagram showing a pSMAHdN628omega-M2GUS binary vector that was used for constructing a construct for inducing a GUS gene using the ALS promoter.

A 2.2-kbp Kpn I/Nco I fragment containing the 5' upstream nucleotide sequence of the rice ALS gene was introduced into a Kpn I/Nco I site of a pSMAHdN628omega-M2GUS binary vector, thereby constructing a construct for inducing a GUS gene using the ALS promoter (FIG. 6).

Figure 7:
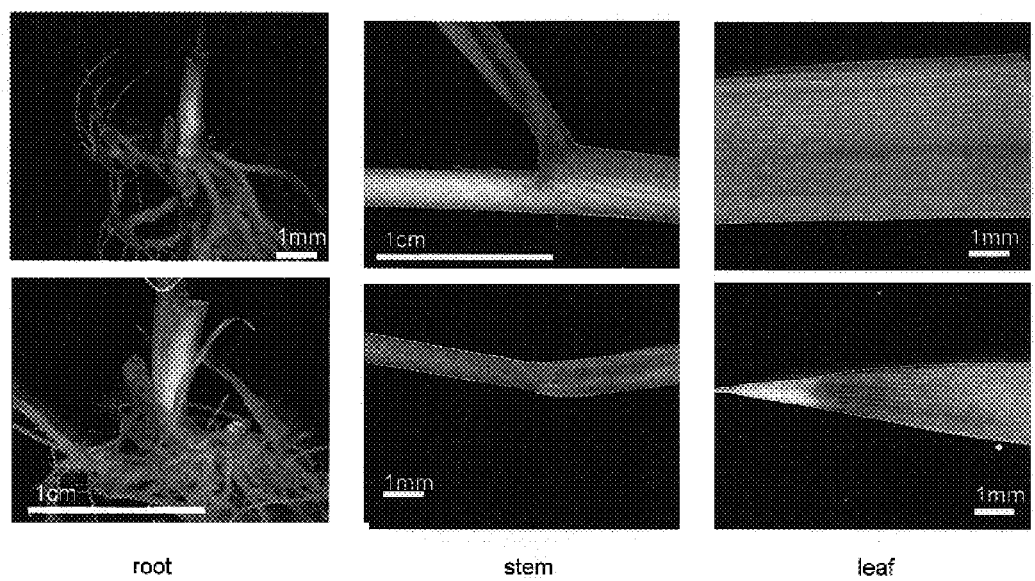
FIG. 7 shows photographs showing localization of GUS activity in 2-week-old seedlings of transformants.

Rice plants were transformed according to the method reported by Toki. Expression of GUS was analyzed by histochemical staining using X-Gluc as a substrate. 2-week-old seedlings of four independent transformants were subjected to analysis of localization of GUS activity. As shown in FIG. 7, while GUS activity was weak in the roots, it was observed throughout the entire plant.

It was revealed by the examples that the promoter comprising the nucleotide sequence shown in SEQ ID NO: 1 induces specific expression in plant tissues other than roots.

Example 5

Expression of Promoter at Each Site Using Transformant

In a manner similar to that of the above method, rice plants were transformed with a vector having an ALS promoter-driven GUS gene and then selected using hygromycin. The three thus selected rice lines (HF1-1, HF1-3, and HF1-4) of the $T_0$ generation and rice plants of the original variety (Nippon-bare) as a control for comparison were cultivated. Specifically, the rice plants were cultivated at a daytime temperature of 30° C. and a nighttime temperature of 20° C. under day length conditions of 13 hours of light and 11 hours of darkness. About 2 months after the start of cultivation, leaves ($10^{th}$ to $12^{th}$ leaves in total), stems (stems including leaf sheaths with $10^{th}$ leaf and $12^{th}$ leaf), and roots were separately sampled from cultivated plants. GUS activity was measured for each site. Each root was cut in half from the foot, and the foot (base) and the tip were measured separately. Subsequently, 5 grains each of immature seeds and the same amount of ripened seeds were sampled from ears (of plants that had developed ears) of each line, and then GUS activity was measured. Before GUS activity measurement, the samples were stored at −80° C., and then the activity was measured within 1 week after sampling.

GUS-specific Activity of Each Site of Transformed Rice

Figure 8:
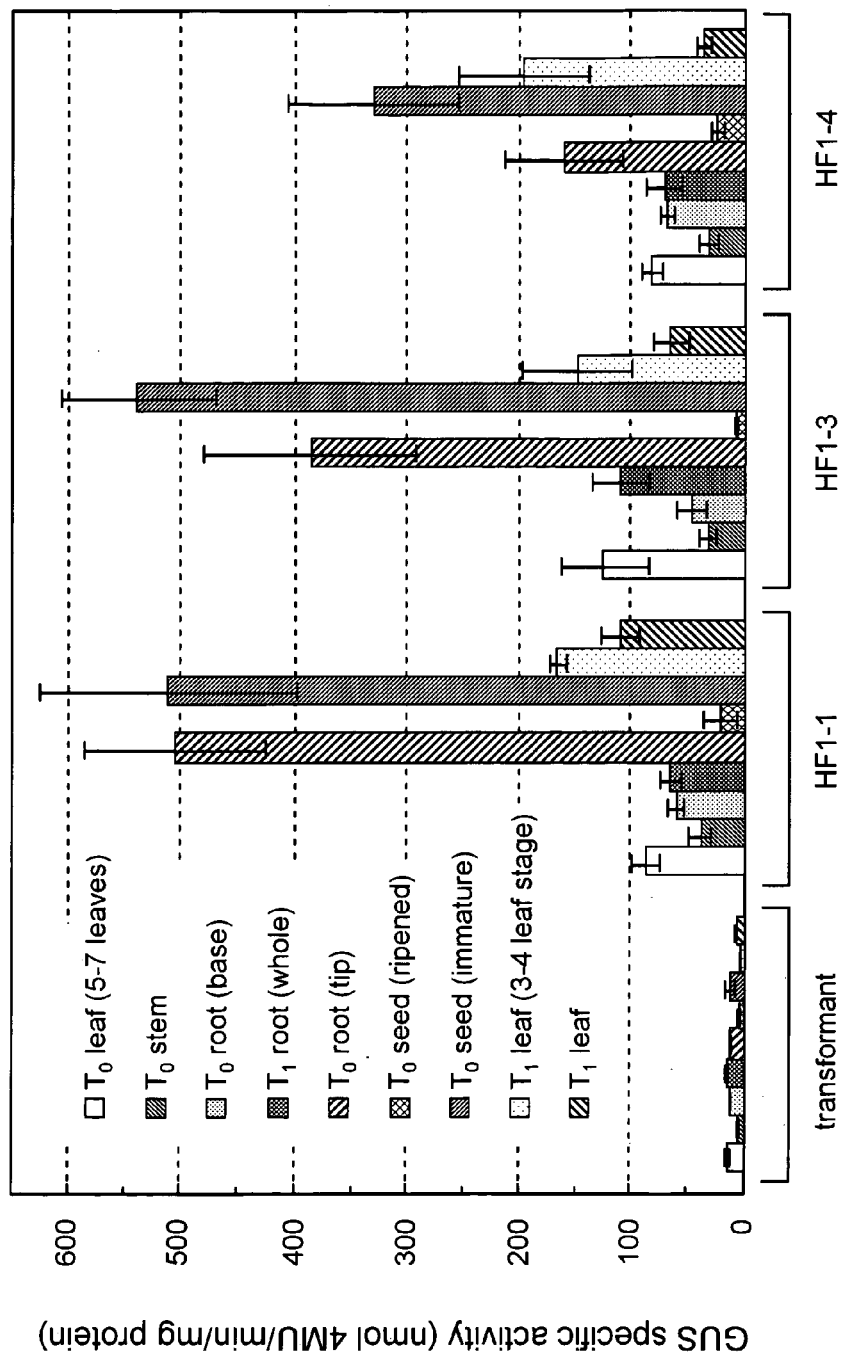
FIG. 8 is a characteristic figure showing the result of measuring GUS activity in transformed rice plants (HF1-1, HF1-3, and HF1-4 lines).

The results of measuring GUS activity in the $T_0$ generation obtained in this example are shown in Table 1 and FIG. 8.

TABLE 1

|  | WT | HF1-1 | HF1-3 | HF1-4 |
| --- | --- | --- | --- | --- |
| Leaf (10th to 12th leaves) | 15.28 ± 2.59 | 85.73 ± 12.98 | 123.46 ± 39.04 | 81.53 ± 9.16 |
| Stem | 5.60 ± 1.14 | 38.73 ± 9.06 | 32.58 ± 6.60 | 32.06 ± 8.30 |
| Root (base) | 12.60 ± 0.47 | 59.34 ± 7.58 | 46.66 ± 12.63 | 67.35 ± 6.58 |
| Root (tip) | 12.60 ± 0.97 | 504.61 ± 79.50 | 385.90 ± 93.37 | 159.60 ± 52.35 |
| Seed (ripened) | 4.87 ± 1.83 | 21.34 ± 14.83 | 8.26 ± 1.18 | 24.43 ± 6.05 |
| Seed (inmature) | 13.13 ± 4.49 | 510.86 ± ##### | 537.49 ± 67.77 | 329.78 ± 75.45 |

Expression of ALS Promoter at Each Site During Seedling Stage 6 plants of the $T_1$ generation obtained from rice transformed plants of each of HF1-1, HF1-3, and HF1-4 lines and rice plants of the original variety (Nippon-bare) as a control for comparison were cultivated. Specifically, the plants were cultivated at a daytime temperature of 30° C. and a nighttime temperature of 25° C. under day length conditions of 16 hours of light and 18 hours of darkness. About 3 weeks after the start of cultivation (corresponding to periods when plants were 3 to 4 weeks old), leaves ($1^{st}$ to $4^{th}$ leaves in total), stems (whole stems including leaf sheaths), and roots (whole roots) were separately sampled from cultivated plants. GUS activity was measured for each site. Before GUS activity measurement, the samples were stored at −80° C., and then the activity was measured within 1 week after sampling.

GUS Extraction, GUS Activity Measurement, and Protein Quantification

The samples were frozen and crushed using liquid nitrogen. 100 mg portions of each of the samples were put into 1.5 ml Eppendorf tubes. 200 μl of the following EX buffer was added to the tube, the solution was centrifuged at 15000 rpm at 4° C. for 5 minutes, and then the supernatant was collected. 10 μl of the collected supernatant was added to 100 μl of the following 4-MUG/EX buffer, followed by 1 hour of incubation at 37° C. A group to which no supernatant had been added was used as a control group. After completion of incubation, 1.4 ml of 0.2 M $Na_2CO_3$ was added to stop the reaction. Fluorescence intensity was then measured at an excitation wavelength of 355 nm and a fluorescence wavelength of 460 nm using a fluorometer (F-2500 spectrophotofluorometer manufactured by Hitachi, Ltd.) (the samples were stored in ice while being light-shielded until measurement.). A calibration curve was prepared using 4-methyl umbelliferone (4-MU). Protein concentration was measured according to attached protocols using a Bio-Rad protein assay kit.

EX Buffer Composition (to Prepare 100 ml of the Buffer)
0.5 M $NaHPO_4$ (pH7.0) 3 ml
0.5 M EDTA 200 μl
0.1% (v/v) TritonX-100
2-mercaptoethanol 71 μl
Add distilled water to result in a volume of 100 ml 4-MUG/EX Buffer
Dissolve 3.2 mg of 4-methylumbelliferyl β-D-glucuronide (4-MUG) in 8 ml of EX buffer (final 4-MUG concentration: 0.4 mg/ml)

In addition, in this Table, each numerical unit represents nmol 4 MU/min/mg protein. Data regarding leaves, stems, and roots are denoted with an average value (of 3 to 4 samples collected from one plant)±standard error. Data regarding seeds are denoted with an average value (of 5 grains collected from one plant)±standard error.

As shown in Table 1 and FIG. 8, in all 3 lines of transformants of the $T_0$ generation, strong GUS activity was confirmed in immature seeds and at the tips of roots following about 2 months of cultivation. However, GUS activity in mature seeds was extremely weak. At root bases and stems following about 2 months of cultivation, GUS activity was not so strong. GUS activity tended to be stronger in leaves than those in root bases and stems. Regarding seeds, since an introduced character segregates according to Mendel's laws, GUS activity data regarding plants having no GUS genes introduced therein may be included in the results in this Table. However, because activity difference between immature seeds and ripened seeds were extremely large, the promoter shown in SEQ ID NO: 1 was thought to be incapable of functioning in seeds as maturation proceeds. Moreover, the above GUS staining suggested that the functionality of this promoter was weak in the roots. However, the results obtained in GUS activity measurement showed that the promoter strongly functioned also in roots, particularly at portions (including vegetative points) where division actively takes place.

The results of measuring GUS activity of the $T_1$ generation in this example are shown in Table 2 and FIG. 8. For GUS activities of $T_1$ plant bodies shown in Table 2 and FIG. 8, data regarding 3 plants from among 6 plants subjected to measurement were employed excluding data regarding plants whose activity was about the same as that of non-transformants (data regarding plants thought to have no GUS genes introduced therein). In addition, since plants having weak GUS activity, which were thought to have no GUS genes introduced therein, were present in all 3 lines, it was determined that the GUS gene had been introduced heterologously in the $T_0$ generation.

TABLE 2

|  | WT | HF1-1 | HF1-3 | HF1-4 |
|---|---|---|---|---|
| Leaf (3rd to 4th leaves) | 3.55 ± 0.66 | 166.02 ± 7.39 | 147.70 ± 48.99 | 195.77 ± 59.75 |
| Stem | 6.83 ± 1.74 | 110.00 ± 16.58 | 64.85 ± 16.04 | 35.59 ± 6.14 |
| Root | 15.33 ± 1.26 | 64.38 ± 8.92 | 109.76 ± 24.74 | 70.38 ± 15.73 |

In addition, data regarding leaves, stems, and roots are denoted with an average value (of 3 plants)±standard error.

As shown in Table 2 and FIG. 8, in both cases of leaves and stems, GUS activity stronger than that in the case of the above $T_0$ generation was confirmed in all 3 lines. Thus, it was considered that the younger the plant bodies, the more strongly the promoter shown in SEQ ID NO: 1 functions. Hence, it was determined that this promoter is a promoter that strongly functions at actively dividing cells.

EFFECT OF THE INVENTION

According to the present invention, a novel promoter preferable for transforming a plant in particular can be provided. The promoter according to the present invention shows specific expression induction, so that it can be broadly used for producing novel transformed plants.

What is claimed is:

1. A method for expressing a coding sequence in a transgenic plant, which comprises: (i) preparing an expression vector comprising a promoter operably linked to the coding sequence, said promoter is selected from the group consisting of (a) a DNA comprising the nucleotide sequence shown in SEQ ID NO: 1 and (b) a DNA comprising the nucleotide sequence from nucleotides 1344 to 2843 of SEQ ID NO: 1; (ii) introducing the expression vector into a plant cell; and (iii) regenerating a transgenic plant from said cell; wherein said transgenic plant expresses said coding sequence under the transcriptional control of said promoter.

2. The method according to claim 1, wherein said DNA comprises nucleotides from 1344 to 2843 of SEQ ID NO: 1.

3. The method for expressing a coding sequence in the plant of claim 1, wherein the coding sequence encodes a drug-resistant acetolactate synthase.

4. A transformant, which is prepared by introducing an expression vector into a plant cell, said expression vector comprising a promoter selected from the group consisting of (a) a DNA comprising the nucleotide sequence shown in SEQ ID NO: 1 and (b) a DNA comprising the nucleotide sequence from nucleotides 1344 to 2843 of SEQ ID NO :1; and wherein (a) and (b) control the transcription of a coding sequence operably linked to said promoter.

5. A transgenic plant or seed obtained from the transformant of claim 4, and wherein said seed comprises the expression vector.

6. The transformant of claim 4, wherein said DNA comprises nucleotides from 1344 to 2843 of SEQ ID NO: 1.

7. The transformant of claim 4, wherein the coding sequence encodes a drug-resistant acetolactate synthase.

* * * * *

SEQUENCE LISTING

<160> NUMBER OF SEQ ID NOS: 6

<210> SEQ ID NO 1
<211> LENGTH: 2843
<212> TYPE: DNA
<213> ORGANISM: Oryza sativa

<400> SEQUENCE: 1

```
agatctccaa tatattcttt ttcaatactt tcctcgcttg ctctagatca taaactaatc    60
aagaattctg cctacttgtt ctgactaaca tttagcttga agatgatgta tagtagtatg   120
acagatcaac cactgacctg aatcacgctc acaggttagg ttcacattat ttgcaagcag   180
atagaatatg cttctatcag agactacacc atctggtgtt caaactaaat gctgataaac   240
atgcgtgcac gagaagccag gatggatgag ttctacatac atgggattag tctacaacca   300
gccttttaac cttggctcaa aaacagaaaa gagaagtaaa aaggaaaacc acaccaggca   360
tagaactcac taactcagca cccttgtttc actaagcact ggcagtctgg cacctatttt   420
ataaaaggta ccttattgtt ccatttctag gagtacatag ttccaaactt ccagctgtat   480
attatcattc cacaaatgaa attccatgga aatatgggcc aaaagctaac aatttgttaa   540
aagagatgta gcagtggcac aaaattgtaa gaccaatgtc accaatcaca tactaaatgg   600
ttgtgtcaag ataagtggct gaataagtct acatgttaac catcaaacct ggtaacaggt   660
acccgtaaag tcttcactcc tcccccttt ctctagtta gcggagacat gacaaccagt   720
catccgatta ggtttatagt ggcattgcaa gcagtcagca aatgaataaa tgaaagaggc   780
aatcttcatg gtcctcttca tcttgtctca catgcgagtt gattttagac caacacggta   840
actcagggga taaaatagat ttgttacaaa tttccaataa gtaagattcc atgaaattgg   900
tgatagtata taatgatttt attgcacaag ctatgcattg cagctactga ttcaacacta   960
ttcagaaaaa aaaagaacaa gtgtatttct ggtaaaactg ttccattcaa aatctagtcc  1020
acgactagtc catgatttgg tcgtgtgaaa acaatggatg cactatatag tctctagtac  1080
tattctattg tactaagcac tatatatagt attataaact acggtttatg gagtagccag  1140
caagacaata agttaacaag aaataaattt aaagtactaa acacaataag ccaattagca  1200
tggtgaaatg atgatttgct atgactaatc tacgactaat tgtgcgactt gctatttggt  1260
```

```
cgagtcgtag ccctctagtc gtctgacttg actgacgtta tgactagtct acgacttgat    1320
aacagcgatc cagatgtctt aagtgatgag gagaagaaag aactaccaga aagtaaacct    1380
tatatgcata gttacataca caggtacact tccgaaggcc ccaatcaatg gaataccata    1440
tgctcttatt aggctattat atggttctgg gtaacaatta aatatatcat gggtgtaccg    1500
ccaatgtgaa attgagaact gcatacacat agccacatta taaatataa atgcactatg    1560 ctcctgatca tggaatgcca accccttatt atcaaaccca aagaagggaa atcccttct    1620 atctcaagca tgcacaatta cctttgttta gcataaatct atcaaatatt gcaatgcaaa    1680
ccttaagcac agatgtcctc cctcttaaat attaatcata atcctcagta aatggacata    1740
cagcataaag tactttaaat taccataggt tgaattggaa atattctttt tagtagctca    1800
cagaaaaatg ggtactaaaa ctaactatta gtaaacataa aagcccctta atgataggag    1860
ggctctacac aagacagtca gtagcatgat aaccacctac aatgttgttc ctacaaataa    1920
aaatactgta gcaatctctt actaagttaa aacatactga ggttctaggg tttaaccata    1980
agtaattaga atatcaaaat agctcaagat tagagaaggt cctacagaaa aacacggtta    2040
tctgcttctc aaatggccta gctacaccgg gcactagcag gatcttaaac agcactaaaa    2100
taagtatctc ccttggtcat caaatcgaaa agaaaatcct acagagtcca cgccttcct    2160 tcccccccact aattaacgaa aagaaacgca gagttccaat taaggagaaa gagatacggg    2220
gtacaacaaa catcgcattc gtctcgtgct agggttttcg ggaggcgggt ctagggttga    2280
ggcaaaaagg gggagggaat tgagcagggg gttaccgcgg tagtcgacgc cggagttgag    2340
cttgacgacg acggggcgcc ccctgatgga cttgaggaag tcggagggcg tcttcaccgc    2400
cccgccgccg ccgccaccgc cgccgccgcc cgagccggac ttctcgccgc cactgctcat    2460
cttgcgctgc gttttgtgcgg gtgcgggtgc gggtgctaga ctgctaggtc tcgcggttgc    2520
atccgcatcc gactttgaga tcgatttttt atcgggttct gtaccctcca cccgttattg    2580
ggactgaccc acctgtcatc ctcatccaat cgactgacac gcgggcccag atcgaccccg    2640
acgtggctgt gtgtcatcct atcccaccga catatgggc ccactgtgac gtggccccac    2700
acgatcccat ccgagccaca catcgcctca cgctgcgtca ccgcgcgcgg acaaaacacc    2760 cacacccca cactctccac ccctctctcc ctctcgccca aacccagaaa ccctcgccgc    2820
cgccgccgcc gccaccaccc acc                                           2843
```

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA PCR primer

<400> SEQUENCE: 2
tgggagaaaa gggtcttagg gtggacat                                        28

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA PCR primer

<400> SEQUENCE: 3
acgtggtgtc gctggtggtt ctta                                            24

<210> SEQ ID NO 4
<211> LENGTH: 1935
<212> TYPE: DNA
<213> ORGANISM: Oryza sativa

<400> SEQUENCE: 4

| | | | | | |
|---|---|---|---|---|---|
| atggctacga | ccgccgcggc | cgcggccgcc | gccctgtccg | ccgccgcgac | ggccaagacc | 60 |
| ggccgtaaga | accaccagcg | acaccacgtc | cttcccgctc | gaggccgggt | ggggcggcg | 120 |
| gcggtcaggt | gctcggcggt | gtccccggtc | acccgccgt | ccccggcgcc | gccgccacg | 180 |
| ccgctccggc | cgtggggcc | ggccgagccc | cgcaagggcg | cggacatcct | cgtggaggcg | 240 |
| ctggagcggt | gcggcgtcag | cgacgtgttc | gcctacccgg | gcggcgcgtc | catggagatc | 300 |
| caccaggcgc | tgacgcgctc | cccggtcatc | accaaccacc | tcttccgcca | cgagcagggc | 360 |
| gaggcgttcg | cggcgtccgg | gtacgcgcgc | cgtccggcc | gcgtcgggt | ctgcgtcgcc | 420 |
| acctccggcc | ccgggcaac | caacctcgtg | tccgcgctcg | ccgacgcgct | gctcgactcc | 480 |
| gtcccgatgg | tcgccatcac | gggccaggtc | ccccgccgca | tgatcggcac | cgacgccttc | 540 |
| caggagacgc | ccatagtcga | ggtcacccgc | tccatcacca | agcacaatta | ccttgtcctt | 600 |
| gatgtggagg | acatccccg | cgtcatacag | gaagccttct | tcctcgcgtc | ctcgggccgt | 660 |
| cctggcccgg | tgctggtcga | catccccaag | gacatccagc | agcagatggc | cgtgccggtc | 720 |
| tgggacacct | cgatgaatct | accagggtac | atcgcacgcc | tgcccaagcc | acccgcgaca | 780 |
| gaattgcttg | agcaggtctt | gcgtctggtt | ggcgagtcac | ggcgcccgat | tctctatgtc | 840 |
| ggtggtggct | gctctgcatc | tggtgacgaa | ttgcgctggt | ttgttgagct | gactggtatc | 900 |
| ccagttacaa | ccactctgat | gggcctcggc | aatttcccca | gtgacgaccc | gttgtccctg | 960 |
| cgcatgcttg | ggatgcatgg | cacggtgtac | gcaaattatg | ccgtggataa | ggctgacctg | 1020 |
| ttgcttgcgt | ttggtgtgcg | gtttgatgat | cgtgtgacag | ggaaaattga | ggcttttgca | 1080 |
| agcagggcca | agattgtgca | cattgacatt | gatccagcag | agattggaaa | gaacaagcaa | 1140 |
| ccacatgtgt | caatttgcgc | agatgttaag | cttgctttac | agggcttgaa | tgctctgcta | 1200 |
| caacagagca | caacaaagac | aagttctgat | tttagtgcat | ggcacaatga | gttggaccag | 1260 |
| cagaagaggg | agtttcctct | ggggtacaaa | acttttggtg | aagagatccc | accgcaatat | 1320 |
| gccattcagg | tgctggatga | gctgacgaaa | ggtgaggcaa | tcatcgctac | tggtgttggg | 1380 |
| cagcaccaga | tgtgggcggc | acaatattac | acctacaagc | ggccacggca | gtggctgtct | 1440 |
| tcggctggtc | tgggcgcaat | gggatttggg | ctgcctgctg | cagctggtgc | ttctgtggct | 1500 |
| aacccaggtg | tcacagttgt | tgatattgat | ggggatggta | gcttcctcat | gaacattcag | 1560 |
| gagctggcat | tgatccgcat | tgagaacctc | cctgtgaagg | tgatggtgtt | gaacaaccaa | 1620 |
| catttgggta | tggtggtgca | attggaggat | aggttttaca | aggcgaatag | ggcgcataca | 1680 |
| tacttgggca | acccggaatg | tgagagcgag | atatatccag | atttttgtgac | tattgctaag | 1740 |
| gggttcaata | ttcctgcagt | ccgtgtaaca | aagaagagtg | aagtccgtgc | cgccatcaag | 1800 |
| aagatgctcg | agactccagg | gccatacttg | ttggatatca | tcgtcccgca | ccaggagcat | 1860 |
| gtgctgccta | tgatcccaat | tggggcgca | ttcaaggaca | tgatcctgga | tggtgatggc | 1920 |
| aggactgtgt | attaa | | | | | 1935 |

<210> SEQ ID NO 5
<211> LENGTH: 1882
<212> TYPE: DNA

<213> ORGANISM: Oryza sativa

<400> SEQUENCE: 5

```
tctataatct gtatgttggc aaagcaccag cccggcctat gtttgacctg aatgacccat      60
aaagagtggt atgcctatga tgtttgtatg tgctctatca ataactaagg tgtcaactat     120
gaaccatatg ctcttctgtt ttacttgttt gatgtgcttg gcatggtaat cctaattagc     180
ttcctgctgt ctaggtttgt agtgtgttgt tttctgtagg catatgcatc acaagatatc     240
atgtaagttt cttgtcctac atatcaataa taagagaata agtacttct  atgcaatagc     300
tctgagttaa gtgtttcaac aatttctgaa cttctgaact tatgtttgct caactgtcat     360
cacacgaagt actctccttg taactacatt ttccccaaga ctttaaatcc cctcagttac     420
agcaaaaaat aaactttgca tctactgttt tccctctctt cggtcgatct tattgggtac     480
tactatagag agaggctgca tgaagtattt ccttttctg  tttagttatg ccgtgtaaat     540
tagcatccat gcaaaataga tgaaaaatca agctattcct gactgctaag gattatttt      600
ggcataatgt attcttatat actccctccg tcccatatta taagggatttt tgagttttg     660
tttatactgt ttgaccactc gtcttattca aaaattttta gaattattat ttatttttt      720
tgtgacttac tttattatct aaagtacttt aagcacaatt ttcgtatttt atatttgcac     780
aaattttttg aataagacga atggtcaaac aatacaaata aaaattcaaa atcccttata     840
atatgggacg gagtatgat  agttggtgaa ctgctacgta ttgccatttg acatttttg      900
gattatgcaa ttttgctgtc tatagtgctc taatcaattc gcaatcccga ccttggagta     960
ttggtctcat ggaacccctc atctgagtaa tctccatatt tgattcgcaa ctgagctgct    1020
gcaagcagca agcctgcaac tgggcattct aggggcgact actgttcgac cacacaaaaa    1080
tccagggaaa gcacaacctc ttatcgatgt acatgaccaa ggagataaca gttgcctcat    1140
catttaaaca tgcctagaca agtagacacg tatccacacc tcaagccata aaattataaa    1200
ttatactacc gtttatcatt ttcctacat  gtattagtgc ctcaaataac cgtaaaaatg    1260
ttaccacatc atgagggtaa tttcataaac agtgctagta atggacacc  aggacattgt    1320
aaccctgat  gtaagtgtgt actacctagg ccaatggaag caatgaaaat gagaaacgaa    1380
ccacgttcaa agtgaaacac agcgggcaca aaactctacc gagaacaaca gcatttttaa    1440
caatacaaag gtctacgtat cattagaagc ctcgttgaaa gacaagtcaa ggtactctgc    1500
caagctcaat cctgatggag gcttgacttg gcctcggtca gatgtatcct tctttgcacg    1560
cagtgattct ggaagccagg acttggatcc atccctgggt atcattatgt tgccaacaat    1620
aggttgcaaa tcccgccatg ggtcatcagt catgcttttg tggtagcgaa ctcttccatc    1680
ttgccatcca gaatagtttt gagtgcctga gccatccctt cccctcttc  cccttgatcc    1740
tgggttgttg tagttgtttt ggcccctccc tcttccataa ggtgagtctg gtctacctct    1800
gggtccatag ttcattcggc cgcctccttg gccaggatta tagtttctgg gtccatagct    1860
aggtggatgt ggataaaggc ct                                              1882
```

<210> SEQ ID NO 6
<211> LENGTH: 1935
<212> TYPE: DNA
<213> ORGANISM: Oryza sativa
<220> FEATURE:
<221> NAME/KEY: CDS
<222> LOCATION: (1)..(1932)

<400> SEQUENCE: 6

-continued

| | | |
|---|---|---|
| atg gct acg acc gcc gcg gcc gcg gcc gcc gcc ctg tcc gcc gcc gcg<br>Met Ala Thr Thr Ala Ala Ala Ala Ala Ala Leu Ser Ala Ala Ala<br>1               5                   10                  15 | 48 | |
| acg gcc aag acc ggc cgt aag aac cac cag cga cac cac gtc ctt ccc<br>Thr Ala Lys Thr Gly Arg Lys Asn His Gln Arg His His Val Leu Pro<br>            20                  25                  30 | 96 | |
| gct cga ggc cgg gtg ggg gcg gcg gcg gtc agg tgc tcg gcg gtg tcc<br>Ala Arg Gly Arg Val Gly Ala Ala Ala Val Arg Cys Ser Ala Val Ser<br>        35                  40                  45 | 144 | |
| ccg gtc acc ccg ccg tcc ccg gcg ccg ccg gcc acg ccg ctc cgg ccg<br>Pro Val Thr Pro Pro Ser Pro Ala Pro Pro Ala Thr Pro Leu Arg Pro<br>    50                  55                  60 | 192 | |
| tgg ggg ccg gcc gag ccc cgc aag ggc gcg gac atc ctc gtg gag gcg<br>Trp Gly Pro Ala Glu Pro Arg Lys Gly Ala Asp Ile Leu Val Glu Ala<br>65                  70                  75                  80 | 240 | |
| ctg gag cgg tgc ggc gtc agc gac gtg ttc gcc tac ccg ggc ggc gcg<br>Leu Glu Arg Cys Gly Val Ser Asp Val Phe Ala Tyr Pro Gly Gly Ala<br>                85                  90                  95 | 288 | |
| tcc atg gag atc cac cag gcg ctg acg cgc tcc ccg gtc atc acc aac<br>Ser Met Glu Ile His Gln Ala Leu Thr Arg Ser Pro Val Ile Thr Asn<br>            100                 105                 110 | 336 | |
| cac ctc ttc cgc cac gag cag ggc gag gcg ttc gcg gcg tcc ggg tac<br>His Leu Phe Arg His Glu Gln Gly Glu Ala Phe Ala Ala Ser Gly Tyr<br>        115                 120                 125 | 384 | |
| gcg cgc gcg tcc ggc cgc gtc ggg gtc tgc gtc gcc acc tcc ggc ccc<br>Ala Arg Ala Ser Gly Arg Val Gly Val Cys Val Ala Thr Ser Gly Pro<br>    130                 135                 140 | 432 | |
| ggg gca acc aac ctc gtg tcc gcg ctc gcc gac gcg ctc ctc gac tcc<br>Gly Ala Thr Asn Leu Val Ser Ala Leu Ala Asp Ala Leu Leu Asp Ser<br>145                 150                 155                 160 | 480 | |
| gtc ccg atg gtc gcc atc acg ggc cag gtc ccc cgc cgc atg atc ggc<br>Val Pro Met Val Ala Ile Thr Gly Gln Val Pro Arg Arg Met Ile Gly<br>                165                 170                 175 | 528 | |
| acc gac gcc ttc cag gag acg ccc ata gtc gag gtc acc cgc tcc atc<br>Thr Asp Ala Phe Gln Glu Thr Pro Ile Val Glu Val Thr Arg Ser Ile<br>            180                 185                 190 | 576 | |
| acc aag cac aat tac ctt gtc ctt gat gtg gag gac atc ccc cgc gtc<br>Thr Lys His Asn Tyr Leu Val Leu Asp Val Glu Asp Ile Pro Arg Val<br>        195                 200                 205 | 624 | |
| ata cag gaa gcc ttc ttc ctc gcg tcc tcg ggc cgt cct ggc ccg gtg<br>Ile Gln Glu Ala Phe Phe Leu Ala Ser Ser Gly Arg Pro Gly Pro Val<br>    210                 215                 220 | 672 | |
| ctg gtc gac atc ccc aag gac atc cag cag cag atg gcc gtg ccg gtc<br>Leu Val Asp Ile Pro Lys Asp Ile Gln Gln Gln Met Ala Val Pro Val<br>225                 230                 235                 240 | 720 | |
| tgg gac acc tcg atg aat cta cca ggg tac atc gca cgc ctg ccc aag<br>Trp Asp Thr Ser Met Asn Leu Pro Gly Tyr Ile Ala Arg Leu Pro Lys<br>                245                 250                 255 | 768 | |
| cca ccc gcg aca gaa ttg ctt gag cag gtc ttg cgt ctg gtt ggc gag<br>Pro Pro Ala Thr Glu Leu Leu Glu Gln Val Leu Arg Leu Val Gly Glu<br>            260                 265                 270 | 816 | |
| tca cgg cgc ccg att ctc tat gtc ggt ggt ggc tgc tct gca tct ggt<br>Ser Arg Arg Pro Ile Leu Tyr Val Gly Gly Gly Cys Ser Ala Ser Gly<br>        275                 280                 285 | 864 | |
| gac gaa ttg cgc tgg ttt gtt gag ctg act ggt atc cca gtt aca acc<br>Asp Glu Leu Arg Trp Phe Val Glu Leu Thr Gly Ile Pro Val Thr Thr<br>    290                 295                 300 | 912 | |
| act ctg atg ggc ctc ggc aat ttc ccc agt gac gac ccg ttg tcc ctg<br>Thr Leu Met Gly Leu Gly Asn Phe Pro Ser Asp Asp Pro Leu Ser Leu<br>305                 310                 315                 320 | 960 | |

```
                                                      -continued cgc atg ctt ggg atg cat ggc acg gtg tac gca aat tat gcc gtg gat    1008
Arg Met Leu Gly Met His Gly Thr Val Tyr Ala Asn Tyr Ala Val Asp
                325                 330                 335 aag gct gac ctg ttg ctt gcg ttt ggt gtg cgg ttt gat gat cgt gtg    1056
Lys Ala Asp Leu Leu Leu Ala Phe Gly Val Arg Phe Asp Asp Arg Val
            340                 345                 350 aca ggg aaa att gag gct ttt gca agc agg gcc aag att gtg cac att    1104
Thr Gly Lys Ile Glu Ala Phe Ala Ser Arg Ala Lys Ile Val His Ile
        355                 360                 365 gac att gat cca gca gag att gga aag aac aag caa cca cat gtg tca    1152
Asp Ile Asp Pro Ala Glu Ile Gly Lys Asn Lys Gln Pro His Val Ser
    370                 375                 380 att tgc gca gat gtt aag ctt gct tta cag ggc ttg aat gct ctg cta    1200
Ile Cys Ala Asp Val Lys Leu Ala Leu Gln Gly Leu Asn Ala Leu Leu
385                 390                 395                 400 caa cag agc aca aca aag aca agt tct gat ttt agt gca tgg cac aat    1248
Gln Gln Ser Thr Thr Lys Thr Ser Ser Asp Phe Ser Ala Trp His Asn
                405                 410                 415 gag ttg gac cag cag aag agg gag ttt cct ctg ggg tac aaa act ttt    1296
Glu Leu Asp Gln Gln Lys Arg Glu Phe Pro Leu Gly Tyr Lys Thr Phe
            420                 425                 430 ggt gaa gag atc cca ccg caa tat gcc att cag gtg ctg gat gag ctg    1344
Gly Glu Glu Ile Pro Pro Gln Tyr Ala Ile Gln Val Leu Asp Glu Leu
        435                 440                 445 acg aaa ggt gag gca atc atc gct act ggt gtt ggg cag cac cag atg    1392
Thr Lys Gly Glu Ala Ile Ile Ala Thr Gly Val Gly Gln His Gln Met
    450                 455                 460 tgg gcg gca caa tat tac acc tac aag cgg cca cgg cag tgg ctg tct    1440
Trp Ala Ala Gln Tyr Tyr Thr Tyr Lys Arg Pro Arg Gln Trp Leu Ser
465                 470                 475                 480 tcg gct ggt ctg ggc gca atg gga ttt ggg ctg cct gct gca gct ggt    1488
Ser Ala Gly Leu Gly Ala Met Gly Phe Gly Leu Pro Ala Ala Ala Gly
                485                 490                 495 gct tct gtg gct aac cca ggt gtc aca gtt gtt gat att gat ggg gat    1536
Ala Ser Val Ala Asn Pro Gly Val Thr Val Val Asp Ile Asp Gly Asp
            500                 505                 510 ggt agc ttc ctc atg aac att cag gag ctg gca ttg atc cgc att gag    1584
Gly Ser Phe Leu Met Asn Ile Gln Glu Leu Ala Leu Ile Arg Ile Glu
        515                 520                 525 aac ctc cct gtg aag gtg atg gtg ttg aac aac caa cat ttg ggt atg    1632
Asn Leu Pro Val Lys Val Met Val Leu Asn Asn Gln His Leu Gly Met
    530                 535                 540 gtg gtg caa ttg gag gat agg ttt tac aag gcg aat agg gcg cat aca    1680
Val Val Gln Leu Glu Asp Arg Phe Tyr Lys Ala Asn Arg Ala His Thr
545                 550                 555                 560 tac ttg ggc aac ccg gaa tgt gag agc gag ata tat cca gat ttt gtg    1728
Tyr Leu Gly Asn Pro Glu Cys Glu Ser Glu Ile Tyr Pro Asp Phe Val
                565                 570                 575 act att gct aag ggg ttc aat att cct gca gtc cgt gta aca aag aag    1776
Thr Ile Ala Lys Gly Phe Asn Ile Pro Ala Val Arg Val Thr Lys Lys
            580                 585                 590 agt gaa gtc cgt gcc gcc atc aag aag atg ctc gag act cca ggg cca    1824
Ser Glu Val Arg Ala Ala Ile Lys Lys Met Leu Glu Thr Pro Gly Pro
        595                 600                 605 tac ttg ttg gat atc atc gtc ccg cac cag gag cat gtg ctg cct atg    1872
Tyr Leu Leu Asp Ile Ile Val Pro His Gln Glu His Val Leu Pro Met
    610                 615                 620 atc cca att ggg ggc gca ttc aag gac atg atc ctg gat ggt gat ggc    1920
Ile Pro Ile Gly Gly Ala Phe Lys Asp Met Ile Leu Asp Gly Asp Gly
```

```
625             630             635             640
agg act gtg tat taa                                     1935
Arg Thr Val Tyr
```